US008119799B2

(12) United States Patent
Binder et al.

(10) Patent No.: US 8,119,799 B2
(45) Date of Patent: Feb. 21, 2012

(54) METHOD FOR THE PRODUCTION OF POLYISOCYANATES COMPRISING ISOCYANURATE GROUPS AND USE THEROF

(75) Inventors: Horst Binder, Lampertheim (DE); Hubert Graf, St. Martin (DE); Frank Braun, Niederkirchen (DE); Bernd Spies, Ludwigshafen (DE); Heinrich Kieslich, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 858 days.

(21) Appl. No.: 10/589,659

(22) PCT Filed: Mar. 9, 2005

(86) PCT No.: PCT/EP2005/002483
§ 371 (c)(1),
(2), (4) Date: Aug. 16, 2006

(87) PCT Pub. No.: WO2005/087828
PCT Pub. Date: Sep. 22, 2005

(65) Prior Publication Data
US 2007/0197759 A1    Aug. 23, 2007

(30) Foreign Application Priority Data
Mar. 12, 2004  (DE) .......................... 10 2004 012 571

(51) Int. Cl.
*C07D 251/00* (2006.01)
*C08G 18/08* (2006.01)

(52) U.S. Cl. .......... 544/222; 544/193; 544/221; 528/48; 528/52; 528/53; 252/182.2; 252/182.21

(58) Field of Classification Search .................... 544/65, 544/351, 180, 193, 345, 222, 221; 521/198, 521/902; 528/52, 53
See application file for complete search history.

(56) References Cited

U.S. PATENT DOCUMENTS

| | | | |
|---|---|---|---|
| 3,862,150 A | | 1/1975 | Bechara et al. |
| 3,954,684 A | * | 5/1976 | Farrissey et al. ............... 521/128 |
| 4,040,992 A | * | 8/1977 | Bechara et al. ................ 521/117 |
| 4,540,781 A | * | 9/1985 | Barsa ............................ 544/193 |
| 5,489,663 A | * | 2/1996 | Brandt et al. ................... 528/52 |
| 5,691,440 A | * | 11/1997 | Katz et al. ........................ 528/52 |
| 6,093,817 A | * | 7/2000 | Kohlstruk et al. ............. 544/193 |
| 6,765,111 B1 | | 7/2004 | Pedain et al. |
| 7,001,973 B2 | * | 2/2006 | Kohlstruk et al. ............... 528/52 |
| 2007/0112085 A1 | * | 5/2007 | Tokumoto et al. ............. 521/128 |

FOREIGN PATENT DOCUMENTS

| | | |
|---|---|---|
| CA | 1335990 | 6/1995 |
| DE | 26 31 733 | 2/1977 |
| DE | 29 16 201 | 10/1980 |
| EP | 0 630 928 | 12/1994 |
| EP | 0 524 201 A1 | 1/1996 |
| JP | 2002 097244 | 4/2002 |
| JP | 2002097244 A * | 4/2002 |
| WO | 93 12153 | 6/1993 |
| WO | 03 020784 | 3/2003 |

OTHER PUBLICATIONS

Chemistry and Technology of Polyols for Polyurethanes. Mihail 2005, Smithers Rapra Technology. p. 84 http://www.knovel.com/web/portal/browse/display?_EXT_KNOVEL_DISPLAY_bookid=2217&VerticalID=0.*

Robins et al., "One Part Adhesives Based on Isocyanate Trimerization", Adhesives, Coating and Sealers Division, vol. 8, pp. 185-216, 1981.

* cited by examiner

*Primary Examiner* — Milton I Cano
*Assistant Examiner* — Michael L Leonard
(74) *Attorney, Agent, or Firm* — Oblon, Spivak, McClelland, Maier & Neustadt, L.L.P.

(57) ABSTRACT

The present invention relates to novel catalysts for preparing polyisocyanates having isocyanurate groups by a partial trimerization of (cyclo)aliphatic diisocyanates.

29 Claims, No Drawings

METHOD FOR THE PRODUCTION OF POLYISOCYANATES COMPRISING ISOCYANURATE GROUPS AND USE THEROF

The present invention relates to a novel process for preparing polyisocyanates having isocyanurate groups by a partial trimerization of (cyclo)aliphatic diisocyanates in the presence of at least one trimerization catalyst from the group of tetrasubstituted ammonium (α-hydroxycarboxylates and to the use of the thus obtainable polyisocyanates having isocyanurate groups as a polyisocyanate component in polyurethane coatings.

Processes for partially or fully trimerizing organic polyisocyanates for preparing polyisocyanates having isocyanurate groups or cellular or compact polyurethanes having isocyanurate groups are known and are described in numerous literature publications.

DE-A 29 16 201 discloses trimerization catalysts composed of a quaternary, optionally substituted 2-hydroxyethylammonium cation and acids as the anion. In these acids R'—COO⁻, R' may be an "optionally oxyalkyl-containing C—C-alkyl radical", but no R' radicals are disclosed for this substitution pattern. This is made more precise in the US equivalent U.S. Pat. No. 4,454,317 in which the R' radical is described as the $C_1$-$C_{12}$-alkyl radical which is optionally substituted by a hydroxyalkyl group, i.e. a hydroxyl group is no closer than in the β-position to the carboxyl group. Only cyanoacetic acid and dichloro-acetic acid are mentioned as substituted acids in the examples.

U.S. Pat. No. 3,862,150 describes salts of tertiary amines and α-substituted carboxylic acids as thermally decomposable catalysts, for example for urethane formation, in which possible α-substituents are nitrile, sulfonyl, sulfuryl, carbonyl, nitro, acetyl and benzoyl groups. The 1,3-dicarbonyl systems or carbonyl-like systems being formed therefrom result in a decarboxylation taking place in a simplified manner, so that such catalysts are readily deactivated, which adversely restricts the temperature range for their usability.

DE-A 26 31 733 discloses optionally substituted 2-hydroxyethylalkylammonium carbonates or carboxylates. Possible carboxylates which are disclosed include salts of hydroxyacetic acid (glycolic acid).

However, a disadvantage of such 2-hydroxyethylalkylammonium carboxylates is their low thermal stressability, so that the use of such salts as catalysts is restricted to a relatively narrow temperature window, and their low catalytic activity which can lead to discolorations of the end product.

WO 93/12153 describes reaction products, effective as trimerization catalysts for isocyanates, of mixtures of carboxylic acids, tertiary amines and epoxides. By way of example, a mixture of lactic acid, bis(3-dimethylamino)formamide and phenyl glycidyl ether is described.

A disadvantage of such reaction products is that to prepare them an up to three-component mixture has to be metered, whose optimal effectiveness depends on precise compliance with the stoichiometry, so that there is the risk of a metering error, and that there could quite possibly be 2-hydroxyethylalkylammonium carboxylates here too, whose disadvantages have already been described above.

WO 03/20784 discloses a process for preparing solid, urethane-modified polyisocyanurate foams in which a commercial trimerization catalyst, for example alkali metal salts of organic acids, if appropriate in the presence of further trimerization catalysts, for example tertiary amines, is used in the presence of a carboxylic acid and in the presence of a blowing agent. The carboxylic acids disclosed are, for example, citric acid, bishydroxypropionic acid, malic acid and preferably lactic acid.

The carboxylic acid does not have any catalytic activity in the trimerization operation, but rather is merely an additive for the foaming operation.

In Advances in Urethane Science and Technology, 1981, 8, 185-216, J. Robins and D. R. O'Keefe describe alkali metal lactate, particularly potassium lactate, as an encapsulated catalyst for trimerization. However, disadvantages are the presence of water, caused by the preparation from the free acid and an alkali metal hydroxide, in the isocyanate, since it can react with the NCO groups to give carbamic acid groups which, after decarboxylation, form amines which lead in turn to the formation of ureas, undesired because they are usually insoluble, and the formation of allophanate, caused by the glycerol solvent used. In addition, the catalysts deactivate rapidly (FIG. 7, ibid.)

JP-A 2002-97244 describes the formation of isocyanurates from isocyanates using a common trimerization catalyst in the presence of ascorbic acid.

However, the addition of 2 components, specifically catalyst and cocatalyst, is again required here, so that metering errors are possible. In addition, JP-A 2002-97244 states in paragraph [0020] that ascorbic acid is insoluble in the reaction medium and has to be dispersed, whereas the isocyanurate catalyst is soluble, which further complicates the metering to achieve optimal action.

It is an object of the present invention to provide a catalyst for preparing substantially colorless isocyanurate-containing polyisocyanates by a very simple process in very good quality and reproducibly irrespective of their preparation, which catalyst can be employed over a wide temperature range and which has a uniform structure.

This object is achieved by a process for preparing isocyanurate-containing polyisocyanates by at least partly trimerizing (cyclo)aliphatic diisocyanates, in which the reaction is carried out in the presence of at least one trimerization catalyst selected from the group of the ammonium salts, substituted by four hydrocarbon radicals, of α-hydroxycarboxylates.

Hydrocarbon radicals are substituents which consist exclusively of carbon and hydrogen atoms.

A preferred embodiment of the invention is a process for preparing polyisocyanates having isocyanurate groups by at least partially trimerizing aliphatic or/and cycloaliphatic diisocyanates in the presence of at least one trimerization catalyst and subsequently, if appropriate, deactivating the trimerization catalyst on attainment of the desired degree of trimerization, in which the trimerization catalyst used is at least one tetrasubstituted ammonium α-hydroxycarboxylate of the formula (I)

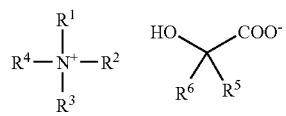

where
$R^1$, $R^2$, $R^3$, $R^4$, $R^5$ and $R^6$ may each independently be the same or different and are each a straight-chain or branched $C_1$- to $C_{20}$-alkyl group, an optionally substituted $C_5$- to $C_{12}$-cycloalkyl group, an optionally substituted $C_7$- to $C_{10}$-aralkyl group, or an optionally substituted $C_6$-$C_{12}$-aryl group, or two or more of the $R^1$ to $R^4$ radicals together form a 4-, 5- or 6-membered alkylene chain or, together with a nitrogen atom, form a 5- or 6-membered ring which may also contain an additional nitrogen or oxygen atom as a bridge member, or together form a multimembered, preferably six-membered, polycyclic system, preferably bicyclic system, which may also contain one or more additional nitrogen atoms, oxygen atoms or oxygen and nitrogen atoms as bridge members, and $R^5$ and $R^6$ may additionally be hydrogen, or $C_1$-$C_{20}$-alkyl or $C_6$- to $C_{12}$-aryl, each optionally interrupted by one or more oxygen and/or sulfur atoms and/or one or more substituted or unsubstituted imino groups, or substituted by functional groups, aryl, alkyl, aryloxy, alkyloxy, halogen, heteroatoms and/or heterocycles.

In these compounds, a straight-chain or branched $C_1$- to $C_{20}$-alkyl group is, for example, methyl, ethyl, propyl, isopropyl, n-butyl, isobutyl, sec-butyl, tert-butyl, pentyl, hexyl, heptyl, octyl, 2-ethylhexyl, 2,4,4-trimethylpentyl, decyl, 1,1-dimethylpropyl, 1,1-dimethylbutyl or 1,1,3,3-tetra-methylbutyl, an optionally substituted $C_5$- to $C_{12}$-cycloalkyl group is cyclopentyl, cyclohexyl, cyclo-octyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxy-cyclohexyl, diethoxycyclohexyl, butylthiocyclohexyl, chlorocyclohexyl, dichlorocyclo-hexyl, dichlorocyclopentyl, or else a saturated or unsaturated bicyclic system, for example norbornyl or norbornenyl, an optionally substituted $C_7$- to $C_{10}$-aralkyl group is, for example, benzyl, 1-phenylethyl, 2-phenylethyl, α,α-dimethylbenzyl, benzhydryl, p-tolylmethyl, 1-(p-butylphenyl)ethyl, o-, m- or p-chlorobenzyl, 2,4-dichlorobenzyl, o-, m- or p-methoxybenzyl or o-, m- or p-ethoxybenzyl, an optionally substituted $C_6$-$C_{12}$-aryl group is, for example, phenyl, 2-, 3- or 4-methyl-phenyl, α-naphthyl or β-naphthyl, $C_1$-$C_{20}$-alkyl optionally interrupted by one or more oxygen and/or sulfur atoms and/or one or more substituted or unsubstituted imino groups or substituted by functional groups, aryl, alkyl, aryloxy, alkyloxy, halogen, heteroatoms and/or heterocycles is, for example, 2-carboxyethyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxy-hexyl, 1-hydroxy-1,1-dimethylmethyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl and $C_6$- to $C_{12}$-aryl optionally interrupted by one or more oxygen atoms and/or sulfur atoms and/or one or more substituted or unsubstituted imino groups or substituted by functional groups, aryl, alkyl, aryloxy, alkyloxy, halogen, heteroatoms and/or hetero-cycles, for example tolyl, xylyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-di-methoxyphenyl, 2,6-dichlorophenyl, 4-bromophenyl, 2- or 4-nitrophenyl, 2,4- or 2,6-di-nitrophenyl, 4-dimethylaminophenyl, 4-acetylphenyl, methoxyethylphenyl or ethoxy-methylphenyl.

Examples of $R^1$ to $R^4$ are in each case independently methyl, ethyl, n-propyl, isopropyl, n-butyl, sec-butyl, tert-butyl, pentyl, hexyl, heptyl, octyl, 2-ethylhexyl, phenyl, α- or β-naphthyl, benzyl, cyclopentyl or cyclohexyl.

When two or more of the $R^1$ to $R^4$ radicals form a ring, these may be, for example, 1,4-butylene, 1,5-pentylene, 3-oxa-1,5-pentylene, 3-aza-1,5-pentylene or 3-methyl-3-aza-1,5-pentylene.

Preferred $R^1$ to $R^4$ radicals are each independently methyl, ethyl, propyl, isopropyl, n-butyl, tert-butyl, phenyl and benzyl, particular preference is given to methyl, ethyl, n-butyl, phenyl and benzyl, very particular preference is given to methyl, ethyl and n-butyl and in particular methyl.

Examples of $R^5$ and $R^6$ are each independently hydrogen, methyl, ethyl, n-propyl, n-butyl, tert-butyl, pentyl, hexyl, heptyl, octyl, 2-ethylhexyl, phenyl, α- or β-naphthyl, benzyl, cyclopentyl, cyclohexyl, hydroxymethyl, 2-hydroxyethyl, 2-carboxyethyl, 2-methoxycarbonylethyl, 2-ethoxycarbonylethyl, 2-n-butoxycarbonylethyl or 2-cyano-ethyl. Preference is given to hydrogen, methyl, ethyl, n-propyl, n-butyl, phenyl, 2-carboxyethyl and 2-hydroxyethyl, particular preference is given to hydrogen, methyl; ethyl, n-butyl and phenyl, very particular preference is given to hydrogen, methyl, ethyl and n-butyl and in particular to hydrogen and methyl.

When the $R^5$ and $R^5$ radicals form a ring, these may be, for example, 1,4-butylene or 1,5-pentylene.

Examples of ammonium cations are tetraoctylammonium, tetramethylammonium, tetraethylammonium, tetra-n-butylammonium, trimethylbenzylammonium, triethyl-benzylammonium, tri-n-butylbenzylammonium, trimethylethylammonium, tri-n-butyl-ethylammonium, triethylmethylammonium, tri-n-butylmethylammonium, diisopropyl-diethylammonium, diisopropylethylmethylammonium, diisopropylethylbenzyl-ammonium, N,N-dimethylpiperidinium, N,N-dimethylmorpholinium, N,N-dimethylpiperazinium or N-methyidiazabicyclo[2.2.2]octane. Preferred alkylammonium ions are tetraoctylammonium, tetramethylammonium, tetraethylammonium and tetra-n-butyl-ammonium, particular preference is given to tetramethylammonium and tetraethyl-ammonium and very particular preference is given to tetramethylammonium.

Ammonium ions containing ring systems are, for example, methylated, ethylated or benzylated piperazines, piperidines, morpholines, quinuclidines or triethylenediamines.

Examples of α-hydroxycarboxylates are, for example, glycolic acid (hydroxyacetic acid), lactic acid, citric acid, 2-methyllactic acid (α-hydroxyisobutyric acid), 2-hydroxy-2-methylbutyric acid, 2-hydroxy-2-ethylbutyric acid, 2-hydroxy-3-methylbutyric acid, 2-hydroxycaproic acid, malic acid, tartaric acid, glucuronic acid, gluconic acid, citramalic acid, saccharic acid, ribonic acid, benzilic acid, quinic acid, mandelic acid, hexahydromandelic acid, 2-hydroxycaproic acid and 3-phenyllactic acid. Preferred α-hydroxycarboxylates are lactic acid, 2-methyllactic acid (α-hydroxyisobutyric acid), 2-hydroxy-2-methylbutyric acid and 2-hydroxycaproic acid, particular preference is given to lactic acid, 2-methyllactic acid (α-hydroxyisobutyric acid) and 2-hydroxycaproic acid and very particular preference is given to lactic acid.

In the case of chiral compounds, it is of no importance to the invention which enantiomer or diastereomer is used, or whether the acids are used in racemic form.

In the context of this document, α-hydroxycarboxylic acids and α-hydroxycarboxylates refer to those carboxylic acids which are substituted by exactly one hydroxyl group (—OH) on a carbon atom bonded directly to a carboxyl group, and their salts respectively. This structural unit may be present once or more than once within a molecule, for example once to six times, preferably once to four times, even more preferably once to three times, in particular once to twice and especially once.

The inventive trimerization catalysts are generally thermally stable even at temperatures above 100° C. and are thus catalytically active over a temperature range of from about 30 to 160° C., whereas acid-base salts of tertiary amines are decomposed even at temperatures around 130° C. (see U.S. Pat. No. 3,862,150, ex. 2), the decomposition reaction setting in even at substantially lower temperatures, and quaternary hydroxyalkylammonium carboxylates can generally only be used at temperatures of from 60 to 80° C. owing to their thermal instability.

However, higher trimerization temperatures, for example above 95° C., are frequently used to trimerize sterically hindered diisocyanates, for example isophorone diisocyanate or 2-butyl-2-ethylpentane 1,5-diisocyanate, and in particular to prepare higher oligomers, since higher space-time yields can thus be achieved. When the inventive tetrasubstituted ammonium α-hydroxycarboxylates are used the reaction rate of the trimerization reaction can be at least retained or even increased compared to commercial trimerization catalysts, preferably N-(2-hydroxypropyl)-N,N,N-trimethyl-ammonium 2-ethylhexanoate (DABCO TMR® from Air Products). In addition, polyisocyanates having isocyanurate groups and extremely low Hazen color numbers (DIN ISO 6271), for example preferably of less than 40 (for HDI), or below 200, preferably below 100 (for IPDI) are also obtained.

As has already been explained, the trimerization catalysts which can be used in accordance with the invention can be prepared by known processes. To prepare tetrasubstituted ammonium α-hydroxycarboxylates of the formula (I), preferably tetraalkylammonium α-hydroxycarboxylates and more preferably trialkylmethyl-ammonium α-hydroxycarboxylates, tertiary amines may be reacted with an alkylating agent, for example alkyl halides, dialkyl carbonates or dialkyl sulfates, in the absence or presence of solvents, for example chlorobenzene, toluene or xylene, at temperatures of appropriately from 100 to 180° C. If appropriate, the reaction may be carried out under pressure when the amine used is gaseous under the reaction conditions.

Preferred alkylating agents are methyl chloride, ethyl chloride, methyl iodide, dimethyl carbonate, diethyl carbonate, di-n-butyl carbonate, dimethyl sulfate and diethyl sulfate, and also benzyl chloride.

Examples of suitable tertiary amines include: trimethylamine, triethylamine, tri-n-butyl-amine, ethyldiisopropylamine, N,N'-dimethylpiperazine, N-methoxyphenylpiperazine, N-methylpiperidine, N-ethylpiperidine, quinuclidine and trialkylamines, for example trimethyl-, triethyl- and tripropylamine, and preferably 1,4-dimethylpiperazine, N,N-dimethylbenzylamine and triethylenediamine.

The tetrasubstituted ammonium ions, obtained after the alkylation, with the alkylating agent as the counterion, for example chloride, iodide, methyl carbonate or methyl sulfate, may then, for example, by treating with an anion exchanger, are then converted in a preferred embodiment to the tetrasubstituted ammonium hydroxide which can then subsequently be reacted with the α-hydroxycarboxylic acid. The equivalent amounts of water which are formed may either be left in the catalyst or may preferably be removed or depleted by treating with drying agent, for example molecular sieve or zeolite, or azeotropic distillation with an entraining agent, for example cyclohexane, benzene or toluene. In general, a water content in the catalyst of below 0.5% by weight is sufficient for use in the inventive reaction and is aimed for.

The presence of water in the reaction generally leads, as a result of hydrolysis of the isocyanates and decarboxylation of the resulting carbamic acids, to amines which in turn react with isocyanates to give sparingly soluble, undesired ureas.

It is also possible to carry out a direct exchange on an ion exchanger column. To this end, a basic ion exchange resin (for example Amberlyst®, Dowex® or Sephadex® type) is activated with potassium hydroxide solution or sodium hydroxide solution and laden with the desired α-hydroxycarboxylic acid. Afterward, the chromatography column is charged with the quaternary ammonium salt and eluted. The eluate contains the desired quaternary ammonium carboxylate. The solvent may be removed by applying vacuum.

In the case of the quaternary ammonium halides, the catalysts can also be obtained in very pure form by cation exchange in solution when the silver carboxylates on which the α-hydroxycarboxylic acids are based are used as reaction partners.

The inventive catalysts can be prepared, for example in a similar manner to the working methods, such as in U.S. Pat. No. 5,691,440, col. 11, line 24-col. 12, line 41.

The alkylation of tertiary amines may be performed, for example, as follows: the tertiary amine, if appropriate in a suitable solvent, for example a $C_1$-$C_4$-alcohol, preferably methanol or ethanol, is reacted with the alkylating agent in super- or substoichiometric or preferably equimolar amounts, for example 0.75-1.25 mol/mol, preferably 0.9-1.1 mol/mol, based on the tertiary amine, if appropriate under elevated pressure, for from 30 minutes to 24 h, at a temperature between room temperature and 120° C., if appropriate at rising temperature in the course of the reaction. On completion of reaction, the volatile constituents are removed by distillation and, if appropriate, washed or recrystallized.

The resulting tetrasubstituted ammonium ion with the counterion of the alkylating agent may then, for example, be exchanged on an anion exchanger laden with hydroxide ions for a hydroxide counterion, as described, for example, in DE-A 25 27 242, p. 6, at the bottom, or ibid., in preparation examples 1 and 2 on p. 13 and 14.

The thus obtained or a commercially available tetrasubstituted ammonium hydroxide may then be reacted with the desired α-hydroxycarboxylic acid to give the inventive catalyst. To this end, for example, the tetrasubstituted ammonium hydroxide is initially charged, for example in a solvent, preferably a solvent which forms an azeotrope with water, for example a $C_1$-$C_4$-alcohol, preferably methanol or ethanol, and to this is slowly added the desired α-hydroxycarboxylic acid, if appropriate likewise in the same solvent or a different solvent. The addition may be effected at from 0 to 100° C., preferably from 0 to 80° C., more preferably from 0 to 60° C., even more preferably from 10 to 40° C. and in particular at room temperature. After any solvent present has been removed together with water of reaction formed, for example by distillation, if appropriate under reduced pressure, the inventive catalyst can be used and may, if appropriate, be taken up in a solvent. Such a solvent may also contain groups reactive toward isocyanate.

The inventive catalyst may be used in bulk, as solution or as suspension.

When the catalyst is used as the solution, depending on the solubility in the solvent used, a solution having a dilution of generally 10-80%, preferably 10-50%, more preferably 15-45% and most preferably 30-40% by weight is established.

The trimerization catalysts used may also be mixtures with other known trimerization catalysts, and these may be mixed in broad ratios, for example in ratios of from 90:10 to 10:90, preferably from 80:20 to 20:80 and more preferably from 60:40 to 40:60.

To prepare the polyisocyanates having isocyanurate groups, the inventive trimerization catalysts, depending on their catalytic activity, are appropriately used in very small effective amounts which can be determined experimentally in a simple manner.

In general, the tetrasubstituted ammonium α-hydroxycarboxylates (I) are used in the process according to the invention in an amount of from 0.002 to 0.05% by weight, preferably from 0.005 to 0.02% by weight, based on the weight of the (cyclo)aliphatic diisocyanates.

The process according to the invention is appropriately carried out at a temperature in the range from 10 to 150° C. and reaction times of 10 min -6 hours, preferably of from 20 min to 3 hours, more preferably of from 20 min to 2 hours. At temperatures above 150° C., discoloration of the polyisocyanates having isocyanurate groups may occur, for example in the case of prolonged reaction times.

When the inventive tetrasubstituted ammonium α-hydroxycarboxylates are used, preference is given to employing reaction temperatures above 50° C., more preferably from 60 to 120° C., and substantially colorless trimerization products are obtained.

The trimerization may be carried out continuously, semi-continuously or batchwise, preferably batchwise.

In general, it is unimportant which components are initially charged or added. Usually, the isocyanate to be trimerized is at least partly, preferably fully, initially charged and the at least one catalyst is added slowly and/or in portions, then brought to the desired reaction temperature, and the remainder of the catalyst is added, if appropriate in portions.

An alternative preparation variant proceeds as follows: a batchwise process is performed in a stirred reactor. The mixture of diisocyanate and catalyst is initially charged typically at approx. 40° C. Afterward, the trimerization is initiated by increasing the temperature of the reaction mixture to from 50 to 140° C., preferably to from 55 to 100° C. Alternatively, the catalyst may also be metered in after the diisocyanate has attained the temperature necessary for the reaction. The trimerization is generally exothermic, the catalyst can be used in pure form. It is also possible to dissolve the catalyst in a suitable solvent and to use it in this form.

The continuous trimerization is appropriately carried out in a reaction coil with continuous, simultaneous metering of diisocyanate and the catalyst at from 50 to 160° C. and within from 30 seconds to 4 hours. A reaction coil having a small diameter leads to the achievement of high flow rates and consequently good mixing. It is also advantageous to heat the diisocyanate/catalyst mixture to from approx. 50 to 60° C. before entry into the reaction coil. For more precise metering and optimal mixing of the catalyst, it is also advantageous to dissolve the catalyst in a suitable solvent. In principle, suitable solvents are those in which the catalyst has a good solubility. The continuous trimerization may also be carried out in a tank battery. Also conceivable is a combination of tank battery and tubular reactor.

Typically, the reaction is carried out in a gas or gas mixture which is inert under the reaction conditions, for example those having an oxygen content of below 2%, preferably below 1%, more preferably below 0.5% by volume; preference is given to nitrogen, argon, helium, nitrogen-noble gas mixtures; particular preference is given to nitrogen.

Once the desired degree of trimerization, i.e. NCO content, or degree of reaction (based on the NCO content before the reaction) of the isocyanurate/(cyclo)aliphatic diisocyanate reaction mixture has been attained, the degree of reaction appropriately being in the range of from 20 to 45% of the NCO groups, preferably from 25 to 35% of the NCO groups, and for which typically reaction times of from 0.05 to 4 hours, preferably from 10 min to 3 hours, are required, the trimerization reaction may be ended, for example, by deactivating the trimerization catalyst.

In addition to monomeric isocyanate, the product comprises compounds which have one or more isocyanurate structures. Compounds of this type are described in the literature.

Suitable deactivating agents are, for example, inorganic acids, for example hydrogen chloride, phosphorous acid or phosphoric acid, carbonyl halides, for example acetyl chloride or benzoyl chloride, sulfonic acids or esters, for example methanesulfonic acid, p-toluenesulfonic acid, methyl or ethyl p-toluenesulfonate, m-chloroperbenzoic acid, and preferably dialkyl phosphates, for example di-2-ethylhexyl phosphate and in particular dibutyl phosphate.

The deactivating agents may, based on the trimerization catalysts, be used in equivalent or excess amounts, and the smallest effective amount, which can be determined experimentally, is preferred simply for economic reasons. For example, the deactivating agent is used in a ratio to the trimerization catalyst of 1-2.5:1 mol/mol, preferably 1-2:1 mol/mol, more preferably 1-1.5:1 mol/mol and very particularly preferably 1-1.2:1 mol/mol.

The addition depends upon the type of the deactivating agent. For instance, hydrogen chloride is preferably passed over the reaction mixture in gaseous form or preferably passed through the reaction mixture, liquid deactivating agents are usually added in substance or as a solution in a solvent inert under the reaction conditions, and solid deactivating agents in substance or as a solution or suspension in a solvent inert under the reaction conditions.

The deactivating agent is generally added at the reaction temperature, but can also be added at lower temperature.

Preference is given to carrying out the process according to the invention without solvent. However, when the (cyclo) aliphatic diisocyanates are trimerized partially in the presence of solvents or diluents, suitable solvents or diluents for this purpose are either inert and nonpolar or inert and polar, for example toluene, xylene, cyclic ethers, carboxylic esters and ketones or mixtures thereof.

The polyisocyanates having isocyanurate groups which are prepared by the process according to the invention may be freed of any solvent or diluent present and/or preferably of excess, unconverted (cyclo)aliphatic diisocyanates in a manner known per se, for example by thin-film distillation at a temperature of from 100 to 180° C., if appropriate under reduced pressure, if appropriate additionally while passing through inert stripping gas, or extraction, so that the polyisocyanates having isocyanurate groups are obtainable with a content of monomeric diisocyanates of, for example, below 1.0% by weight, preferably below 0.5% by weight, more preferably below 0.3% by weight, even more preferably below 0.2% by weight and in particular not more than 0.1% by weight.

Without removal of the excess monomeric diisocyanates, the polyisocyanates having isocyanurate groups are suitable, for example, for preparing PU foams, cellular or compact elastomers, casting compositions and adhesives. The monomer-free and monomer-containing polyisocyanates having isocyanurate groups may also be modified in a manner known per se by introducing, for example, urethane, allophanate, urea, biuret and/or carbodiimide groups, and/or the isocyanates may be capped with suitable capping agents, for example ε-caprolactam, dimethyl malonate, ethyl acetoacetate or aromatic hydroxyl groups.

The process according to the invention can be used to trimerize any organic diisocyanates having aliphatic, cycloaliphatic or aliphatic and cycloaliphatic isocyanate groups or mixtures thereof.

Suitable aliphatic diisocyanates have advantageously from 3 to 16 carbon atoms, preferably from 4 to 12 carbon atoms, in the linear or branched alkylene radical, and suitable cycloaliphatic diisocyanates have advantageously from 4 to 18 carbon atoms, preferably from 6 to 15 carbon atoms, in the cycloalkylene radical. Examples include: 1,4-diisocyanatobutane, 2-ethyl-1,4-diisocyanatobutane, 1,5-diisocyanatopentane, 2-methyl-1,5-diisocyanatopentane, 2,2-dimethyl-1,5-diisocyanatopentane, 2-propyl-2-ethyl-1,5-diisocyanatopentane, 2-butyl-2-ethyl-1,5-diisocyanatopentane, 2-alkoxy-methylene-1,5-diisocyanatopentane, 3-methyl-, 3-ethyl-1,5-diisocyanatopentane, hexamethylene 1,6-diisocyanate, 2,4,4- or 2,2,4-trimethylhexamethylene 1,6-diiso-cyanate, 1,7-diisocyanatoheptane, 1,8-diisocyanatooctane, 1,10-diisocyanatodecane, 1,12-diisocyanatododecane, 4,4'-diisocyanatodicyclohexylmethane, 2,4'-diisocyanatodicyclohexylmethane, and also mixtures of the diisocyanatodicyclohexylmethane isomers, 1,3-diisocyanatocyclohexane and also isomer mixtures of diisocyanatocyclo-hexanes and 1-isocyanato-3-isocyanatomethyl-3,5,5-trimethylcyclohexane. The (cyclo)aliphatic diisocyanates used are preferably hexamethylene 1,6-diisocyanate, isomeric aliphatic diisocyanates having 6 carbon atoms in the alkylene radical and mixtures thereof, 2-butyl-2-ethyl-1,5-diisocyanatopentane and 1-isocyanato-3-isocyanatomethyl-3,5,5-trimethylcyclohexane; particular preference is given to hexamethylene 1,6-diisocyanate and 1-isocyanato-3-isocyanatomethyl-3,5,5-trimethyl-cyclohexane and mixtures thereof, for example in a ratio of 10:90-90:10, preferably 20:80-80:20 and more preferably 33:67-67:33.

It will be appreciated that the inventive catalysts also catalyze the trimerization of aromatic isocyanates, but are preferred for (cyclo)aliphatic isocyanates.

The inventive novel trimerization catalysts may be used for the trimerization of (cyclo)aliphatic diisocyanates prepared by any processes, for example by a phosgene-free process route or one proceeding with the use of phosgene.

The (cyclo)aliphatic diisocyanates which can be used in accordance with the invention may be prepared by any processes, for example by phosgenating the appropriate diamines and thermally dissociating the dicarbamoyl chlorides formed as an intermediate. (Cyclo)aliphatic diisocyanates prepared by phosgene-free processes do not contain any chlorine compounds as by-products and therefore contain, as a result of the preparation, a fundamentally different by-product spectrum.

It will be appreciated that mixtures of isocyanates which have been prepared by the phosgene process and by phosgene-free processes may also be used.

It has been found that the trimerization catalysts which can be used in accordance with the invention have good catalytic activity in the trimerization of (cyclo)aliphatic diisocyanates, even those prepared by the phosgene process, and result in polyisocyanates having isocyanurate groups which have a low color number.

The (cyclo)aliphatic diisocyanates which can be used in the process according to the invention and are obtainable by a phosgene-free process and especially by thermal dissociation of (cyclo)aliphatic dicarbamic esters are not restricted, and preference is given in particular to selecting diisocyanates obtainable by thermal dissociation of (cyclo)aliphatic dicarbamic esters from the group of hexamethylene 1,6-diisocyanate, 2-butyl-2-ethylpentamethylene 1,5-diisocyanate and 1-isocyanato-3-isocyanatomethyl-3,5,5-trimethylcyclohexane.

In a preferred embodiment of the invention, isocyanates are used which have a total chlorine content of 100 ppm by weight or less, preferably 80 ppm by weight or less.

Polyisocyanates having isocyanurate groups and prepared by these process variants are suitable preferentially for producing polyurethane coatings, for example textile and leather coatings, for polyurethane dispersions and adhesives, and find use in particular as a polyisocyanate component in one- and two-component polyurethane systems for high-grade, weather-resistant polyurethane coatings and high-solids coatings.

ppm and percentage data used in this document relate, unless stated otherwise, to percentages by weight and ppm by weight.

The examples which follow are intended to illustrate the invention, but not restrict it to these examples.

EXAMPLES

The tetrasubstituted α-hydroxycarboxylates were prepared by reacting the α-hydroxy-carboxylic acid with a tetrasubstituted ammonium hydroxide in methanolic solution. The methanolic carboxylic acid solution was initially charged and the tetrasubstituted ammonium hydroxide, dissolved in methanol, was added dropwise within 30 min. On completion of addition of the ammonium hydroxide, the mixture was stirred at approx. 40° C. for a further 1 hour. Subsequently, water of reaction formed and other volatile constituents were removed on a rotary evaporator. The colorless residue was dissolved in suitable solvents, such as ethyl diglycol or ethylene glycol. It is also possible to recrystallize the carboxylate from suitable solvents, such as ethyl acetate.

Trimerization of HDI, general method for trimerizing isocyanates

For the experiments below, halogen-free hexamethylene diisocyanate (HDI) was used, unless stated otherwise.

Comparative Example 1

100 g of hexamethylene diisocyanate were initially charged under a nitrogen blanket at 80° C. and 50 ppm of DABCO-TMR (DABCO-TMR =N-(2-hydroxypropyl)-N,N,N-tri-methylammonium 2-ethylhexanoate) were added with stirring within approx. 30 min and the mixture was stirred for a further 20 min. The NCO value fell to 37.2%. The reaction was then with bis(2-ethylhexyl)phosphate and the reaction product degassed in a thin-film evaporator at 140° C.

After the degassing, a color number of 53 Hz was measured; the product had an NCO value of 20.9%

Example 1

100 g of hexamethylene diisocyanate were processed as under comparative example 1, but the trimerization catalyst used was the carboxylate of tetramethylammonium hydroxide with 2-hydroxypropionic acid. After the addition of 50 ppm of this catalyst and a total reaction time of 35 min, an NCO value of 27% was measured. The reaction was then terminated with bis(2-ethylhexyl)phosphate.

After the distillative workout, the NCO value was 19.0%. A very light product having a color number of 30 Hz was obtained.

Example 2

100 g of hexamethylene diisocyanate were processed as under comparative example 1, but the trimerization catalyst used was the carboxylate of tetramethylammonium hydroxide with 2-ethyl-2-hydroxybutyric acid. After the addition of 50 ppm of this catalyst and a total reaction time of 50 min, an NCO value of 39.0% was measured. The reaction was then terminated with diethylhexyl phosphate.

After the distillative workout, the NCO value was 21.2%. A very light product having a color number of 21 Hz was obtained.

Example 3

100 g of hexamethylene diisocyanate were processed as under comparative example 1, but the trimerization catalyst used was the carboxylate of tetramethylammonium hydroxide with 2-hydroxyisocaproic acid. After the addition of 50 ppm of this catalyst and a total reaction time of 35 min, an NCO value of 27% was measured. The reaction was then terminated with bis(2-ethylhexyl)phosphate. After the distillative workout, the NCO value was 20.7%. A very light product having a color number of 30 Hz was obtained.

Example 4

HDI from a phosgene process was used.

100 g of hexamethylene diisocyanate were processed as under comparative example 1, but the trimerization catalyst used was the carboxylate of tetramethylammonium hydroxide with 2-ethyl-2-hydroxybutyric acid. After the addition of 35 ppm of this catalyst and a total reaction time of 40 min, an NCO value of 26.5% was measured. The reaction was then terminated with bis(2-ethylhexyl)phosphate.

After the distillative workout, the NCO value was 21.2%. A very light product having a color number of 17 Hz was obtained.

Comparative Example 2

100 g of hexamethylene diisocyanate from a phosgene process having a total chlorine content of 25 ppm were initially charged under a nitrogen blanket at 80° C. and 50 ppm of DABCO-TMR (DABCO-TMR=N-(2-hydroxypropyl)-N,N,N-trimethylammonium 2-ethylhexanoate) were added with stirring within approx. 30 min and the mixture was stirred for a further 20 min. The NCO value fell to 36.8%. The reaction was then with bis(2-ethylhexyl)phosphate and the reaction product degassed in a thin-film evaporator at 140° C.

After the degassing, a color number of 61 Hz was measured; the product had an NCO value of 21.5%.

Trimerization of IPDI

Comparative Example 3

750 g of freshly distilled isophorone diisocyanate were initially charged and heated to 80° C. with supply of $N_2$.

While simultaneously introducing nitrogen, DACBO TMR® was added in portions. After 900 ppm of this catalyst had been added and a total reaction time of 2 hours, an NCO value of 32% was measured in the reaction solution. The reaction was then terminated with bis(2-ethylhexyl)phosphate.

After the distillative workout, the NCO value was 17.2%. A strongly colored product having a color number of 800 Hz was obtained (measured 70% in butyl acetate).

Example 5

750 g of freshly distilled isophorone diisocyanate were initially charged and heated to 80° C. While simultaneously supplying nitrogen, 160 ppm of the carboxylate of tetramethylammonium hydroxide with 2-ethyl-2-hydroxybutyric acid were added in portions. After a total reaction time of 2 hours, an NCO value of 32.8% in the reaction solution was measured. The reaction was then terminated with bis(2-ethylhexyl)phosphate.

After the distillative workout, the NCO value was 17.1%. A slightly yellowish-colored product having a color number of 180 Hz was obtained (measured 70% in butyl acetate).

Example 6

750 g of freshly distilled isophorone diisocyanate were initially charged and heated to 80° C. While simultaneously supplying nitrogen, 160 ppm of the carboxylate of tetramethylammonium hydroxide with 2-hydroxypropionic acid were added in portions. After a total reaction time of 2 hours, an NCO value of 26.1% in the reaction solution was measured. The reaction was then terminated with bis(2-ethylhexyl)phosphate.

After the distillative workout, the NCO value was 17.3%. A light-colored product having a color number of 92 Hz was obtained (measured 70% in butyl acetate).

What is claimed is:

1. A process for preparing isocyanurate-containing polyisocyanates by at least partly trimerizing (cyclo)aliphatic diisocyanates, which comprises carrying out the reaction in the presence of at least one ammonium salt trimerization catalyst, substituted by four hydrocarbon radicals, of α-hydroxy-carboxylates, wherein said reaction is carried out in a gas or gas mixture which is inert under the reaction conditions wherein the said gas or gas mixture which is inert under the reaction conditions has a total oxygen content of below 2% by volume and wherein said at least one trimerization catalyst is at a concentration ranging from 0.002 to 0.05% by weigh based on the weight of the (cyclo)aliphatic diisocyanates.

2. The process according to claim 1, wherein the ammonium ion is selected from the group consisting of tetraoctylammonium, tetramethylammonium, tetraethylammonium, tetra-n-butyl ammonium, trimethylbenzylammonium, triethylbenzylammonium, tri-n-butylbenzylammonium, trimethylethylammonium, tri-n-butylethylammonium, triethylmethylammonium, tri-n-butylmethylammonium, diisopropyldiethylammonium, diisopropylethylmethylammonium, diisopropylethylbenzylammonium, N,N-dimethylpiperidinium, N,N-dimethylmorpholinium, N,N-di-methylpiperazinium and N-methyldiazabicyclo[2.2.2]octane.

3. The process according to claim 1, wherein the α-hydroxycarboxylate ion is an anion of an acid is selected from the group consisting of glycolic acid (hydroxyacetic acid), lactic acid, citric acid, 2-methyllactic acid (α-hydroxyisobutyric acid), 2-hydroxy-2-methylbutyric acid, 2-hydroxy-2-ethylbutyric acid, 2-hydroxy-3-methylbutyric acid, 2-hydroxycaproic acid, malic acid, tartaric acid, glucuronic acid, gluconic acid, citramalic acid, saccharic acid, ribonic acid, benzilic acid, quinic acid, mandelic acid, hexahydromandelic acid, 2-hydroxycaproic acid and 3-phenyllactic acid.

4. The process according to claim 1, wherein the ammonium salt trimerization catalyst is deactivated after the desired degree of trimerization has been attained.

5. The process according to claim 4, wherein the ammonium salt trimerization catalyst is deactivated with dibutyl phosphate or di(2-ethylhexyl)phosphate.

6. The process according to claim 1, wherein the diisocyanates have a total chlorine content of less than 100 ppm by weight.

7. The process according to claim 1, wherein the diisocyanate is 1-isocyanato-3-isocyanato-methyl-3,5,5-trimethyl-cyclohexane.

8. The process according to claim 1, wherein the said gas or gas mixture which is inert under the reaction conditions has a total oxygen content of below 1% by volume.

9. The process according to claim 1, wherein the said gas or gas mixture which is inert under the reaction conditions has a total oxygen content of below 0.5% by volume.

10. The process according to claim 1, wherein the said gas or gas mixture which is inert under the reaction conditions is selected from the group consisting of nitrogen, argon, helium, and a nitrogen-noble gas mixture.

11. The process according to claim 1, wherein the said gas or gas mixture which is inert under the reaction conditions is nitrogen.

12. A process for preparing isocyanurate-containing polyisocyanates by at least partly trimerizing (cyclo)aliphatic diisocyanates, which comprises employing, as the ammonium salt trimerization catalyst, at least one compound of the formula (I)

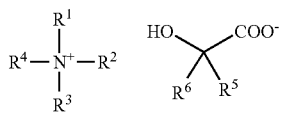

where
$R^1$, $R^2$, $R^3$, $R^4$, $R^5$ and $R^6$ may each independently be the same or different and are each a straight-chain or branched $C_1$- to $C_{20}$-alkyl group, an optionally substituted $C_5$- to $C_{12}$-cycloalkyl group, an optionally substituted $C_7$- to $C_{10}$-aralkyl group, or an optionally substituted $C_6$-$C_{12}$-aryl group, or
two or more of the $R^1$ to $R^4$ radicals together form a 4-, 5- or 6-membered alkylene chain or, together with a nitrogen atom, form a 5- or 6-membered ring which optionally contains an additional nitrogen or oxygen atom as a bridge member, or together form a multimembered, polycyclic system, which optionally contains one or more additional nitrogen atoms, oxygen atoms or oxygen and nitrogen atoms as bridge members, and
$R^5$ and $R^6$ may additionally be hydrogen, or $C_1$-$C_{20}$-alkyl or $C_6$- to $C_{12}$-aryl, each optionally interrupted by one or more oxygen and/or sulfur atoms and/or one or more substituted or unsubstituted imino groups, or substituted by functional groups, aryl, alkyl, aryloxy, alkyloxy, halogen, heteroatoms and/or heterocycles.

13. The process according to claim 12, wherein the $R^1$ to $R^4$ radicals are each independently selected from the group consisting of methyl, ethyl, propyl, isopropyl, n-butyl, tert-butyl, phenyl and benzyl.

14. The process according to claim 12, wherein the $R^5$ and $R^6$ radicals are each independently selected from the group consisting of hydrogen, methyl, ethyl, n-propyl, n-butyl, phenyl, 2-carboxyethyl and 2-hydroxyethyl.

15. A process for preparing isocyanurate-containing polyisocyanates by at least partly trimerizing a halogen-free hexamethyene diisocyanate, which comprises carrying out the reaction in the presence of at least one ammonium salt trimerization catalyst, substituted by four hydrocarbon radicals, of α-hydroxy-carboxylates, wherein said reaction is carried out in a gas or gas mixture which is inert under the reaction conditions wherein the said gas or gas mixture which is inert under the reaction conditions has a total oxygen content of below 2% by volume and wherein said at least one trimerization catalyst is at a concentration ranging from 0.002 to 0.05% by weigh based on the weight of the (cyclo)aliphatic diisocyanates.

16. The process according to claim 15, wherein the ammonium ion is selected from the group consisting of tetraoctylammonium, tetramethylammonium, tetraethylammonium, tetra-n-butylammonium, trimethylbenzylammonium, triethylbenzylammonium, tri-n-butylbenzylammonium, trimethylethylammonium, tri-n-butylethylammonium, triethylmethylammonium, tri-n-butylmethylammonium, diisopropyldiethylammonium, diisopropylethylmethylammonium, diisopropylethylbenzylammonium, N,N-dimethylpiperidinium, N,N-dimethylmorpholinium, N,N-di-methylpiperazinium and N-methyldiazabicyclo[2.2.2]octane.

17. The process according to claim 15, wherein the α-hydroxycarboxylate ion is an anion of an acid is selected from the group consisting of glycolic acid (hydroxyacetic acid), lactic acid, citric acid, 2-methyllactic acid (α-hydroxyisobutyric acid), 2-hydroxy-2-methylbutyric acid, 2-hydroxy-2-ethylbutyric acid, 2-hydroxy-3-methylbutyric acid, 2-hydroxycaproic acid, malic acid, tartaric acid, glucuronic acid, gluconic acid, citramalic acid, saccharic acid, ribonic acid, benzilic acid, quinic acid, mandelic acid, hexahydromandelic acid, 2-hydroxycaproic acid and 3-phenyllactic acid.

18. The process according to claim 15, wherein the ammonium salt trimerization catalyst is deactivated after the desired degree of trimerization has been attained.

19. The process according to claim 15, wherein the ammonium salt trimerization catalyst is deactivated with dibutyl phosphate or di (2-ethylhexyl)phosphate.

20. The process according to claim 15, wherein the halogen-free hexamethyene diisocyanate has a total chlorine content of less than 100 ppm by weight.

21. The process according to claim 15, wherein the halogen-free hexamethyene diisocyanate is hexamethylene 1,6-diisocyanate.

22. A polyisocyanate component in one- and two-component polyurethane systems for high-grade, weather-resistant polyurethane coatings and high-solids coatings comprising a polyisocyanates prepared by the process of claim 15.

23. The process according to claim 15, wherein the said gas or gas mixture which is inert under the reaction conditions has a total oxygen content of below 1% by volume.

24. The process according to claim 15, wherein the said gas or gas mixture which is inert under the reaction conditions has a total oxygen content of below 0.5% by volume.

25. The process according to claim 15, wherein the said gas or gas mixture which is inert under the reaction conditions is selected from the group consisting of nitrogen, argon, helium, and a nitrogen-noble gas mixture.

26. The process according to claim 15, wherein the said gas or gas mixture which is inert under the reaction conditions is nitrogen.

27. A process for preparing isocyanurate-containing polyisocyanates by at least partly trimerizing a halogen-free hexamethyene diisocyanate, which comprises employing, as the ammonium salt trimerization catalyst, at least one compound of the formula (I)

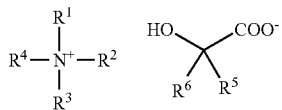

where $R^1$, $R^2$, $R^3$, $R^4$, $R^5$ and $R^6$ may each independently be the same or different and are each a straight-chain or branched $C_1$- to $C_{20}$-alkyl group, an optionally substituted $C_5$- to $C_{12}$-cycloalkyl group, an optionally substituted $C_7$- to $C_{10}$-aralkyl group, or an optionally substituted $C_6$-$C_{12}$-aryl group, or two or more of the $R^1$ to $R^4$ radicals together form a 4-, 5- or 6-membered alkylene chain or, together with a nitrogen atom, form a 5- or 6-membered ring which optionally contains an additional nitrogen or oxygen atom as a bridge member, or together form a multimembered, polycyclic system, which optionally contains one or more additional nitrogen atoms, oxygen atoms or oxygen and nitrogen atoms as bridge members, and $R^5$ and $R^6$ may additionally be hydrogen, or $C_1$-$C_{20}$-alkyl or $C_6$- to $C_{12}$-aryl, each optionally interrupted by one or more oxygen and/or sulfur atoms and/or one or more substituted or unsubstituted imino groups, or substituted by functional groups, aryl, alkyl, aryloxy, alkyloxy, halogen, heteroatoms and/or heterocycles.

28. The process according to claim 27, wherein the $R^1$ to $R^4$ radicals are each independently selected from the group consisting of methyl, ethyl, propyl, isopropyl, n-butyl, tert-butyl, phenyl and benzyl.

29. The process according to claim 27, wherein the $R^5$ and $R^6$ radicals are each independently selected from the group consisting of hydrogen, methyl, ethyl, n-propyl, n-butyl, phenyl, 2-carboxyethyl and 2-hydroxyethyl.

* * * * *